(12) United States Patent
Lampropoulos et al.

(10) Patent No.: US 8,485,986 B2
(45) Date of Patent: Jul. 16, 2013

(54) BIOPSY COLLECTION DEVICE AND RELATED METHODS

(75) Inventors: Fred P. Lampropoulos, Salt Lake City, UT (US); Jim Mottola, Salt Lake City, UT (US); Gregory R. McArthur, Sandy, UT (US)

(73) Assignee: Merit Medical Systems, Inc., South Jordan, UT (US)

( * ) Notice: Subject to any disclaimer, the term of this patent is extended or adjusted under 35 U.S.C. 154(b) by 642 days.

(21) Appl. No.: 12/796,478

(22) Filed: Jun. 8, 2010

(65) Prior Publication Data

US 2011/0301496 A1    Dec. 8, 2011

(51) Int. Cl.
*A61B 10/02* (2006.01)

(52) U.S. Cl.
USPC ............................ 600/562; 210/448; 210/499

(58) Field of Classification Search
USPC ........ 600/562, 565, 566; 435/297.1; 210/448, 210/499
See application file for complete search history.

(56) References Cited

U.S. PATENT DOCUMENTS

| | | | | |
|---|---|---|---|---|
| 3,476,144 A * | 11/1969 | Krantz | ............................ | 433/92 |
| 3,933,652 A * | 1/1976 | Weichselbaum et al. | ..... | 210/446 |
| 3,938,505 A * | 2/1976 | Jamshidi | ........................ | 600/566 |
| 4,083,706 A * | 4/1978 | Wiley | ............................. | 433/92 |
| 4,366,822 A | 1/1983 | Altshuler | | |
| 4,685,472 A * | 8/1987 | Muto | ............................. | 600/573 |
| 4,813,931 A * | 3/1989 | Hauze | ........................... | 600/573 |
| 4,886,492 A * | 12/1989 | Brooke | ........................ | 604/541 |
| 4,957,492 A * | 9/1990 | McVay | ........................ | 600/573 |
| 5,000,854 A | 3/1991 | Yang | | |
| 5,079,170 A | 1/1992 | Rosman et al. | | |
| 5,139,031 A | 8/1992 | Guirguis | | |
| 5,215,536 A | 6/1993 | Lampropoulos et al. | | |
| 5,256,160 A * | 10/1993 | Clement | ....................... | 604/319 |
| 5,352,410 A | 10/1994 | Hansen et al. | | |
| 5,471,994 A * | 12/1995 | Guirguis | ....................... | 600/573 |
| 5,630,939 A * | 5/1997 | Bulard et al. | ................. | 210/448 |
| 5,685,864 A | 11/1997 | Shanley et al. | | |
| 5,766,134 A * | 6/1998 | Lisak et al. | .................... | 600/562 |
| 5,788,863 A * | 8/1998 | Milunic | ........................ | 210/651 |
| 6,083,175 A * | 7/2000 | Lundgren | ..................... | 600/562 |
| 6,197,289 B1 | 3/2001 | Wirt et al. | | |
| 6,299,763 B1 * | 10/2001 | Ashman | ........................ | 210/499 |
| 6,478,808 B2 * | 11/2002 | Nowakowski | ............... | 606/214 |
| 6,989,022 B2 * | 1/2006 | Nowakowski | ................ | 606/214 |
| 7,204,810 B2 * | 4/2007 | Hynes et al. | .................. | 600/562 |
| 7,510,686 B2 * | 3/2009 | Schluter | ........................ | 436/174 |
| 7,981,380 B2 * | 7/2011 | Solazzi | ......................... | 600/562 |
| 2003/0173284 A1 | 9/2003 | Baker | | |
| 2004/0241874 A1 | 12/2004 | Abdel-Rehim | | |
| 2009/0259160 A1 | 10/2009 | Josephs | | |
| 2011/0004119 A1* | 1/2011 | Hoffa et al. | .................... | 600/566 |

* cited by examiner

*Primary Examiner* — Brian Szmal
*Assistant Examiner* — Emily Lloyd
(74) *Attorney, Agent, or Firm* — Stoel Rives LLP

(57) ABSTRACT

A biopsy collection device may include a filter located distally of an aspiration device to collect a biological sample aspirated from a patient. The biological sample may be accessible to a clinician without the need to expel the sample from the aspiration device. The filter may be disposed in a filter housing that is in fluid communication with the aspiration device and the vasculature of a patient.

17 Claims, 8 Drawing Sheets

BIOPSY COLLECTION DEVICE AND RELATED METHODS

TECHNICAL FIELD

The present disclosure relates generally to biopsy collection devices. More specifically, the present disclosure relates to biopsy collection devices for aspirating a biological sample comingled with bodily fluid of a patient.

BRIEF DESCRIPTION OF THE DRAWINGS

The embodiments disclosed herein will become more fully apparent from the following description and appended claims, taken in conjunction with the accompanying drawings. These drawings depict only typical embodiments, which will be described with additional specificity and detail through use of the accompanying drawings in which:

DETAILED DESCRIPTION

Figure 1:
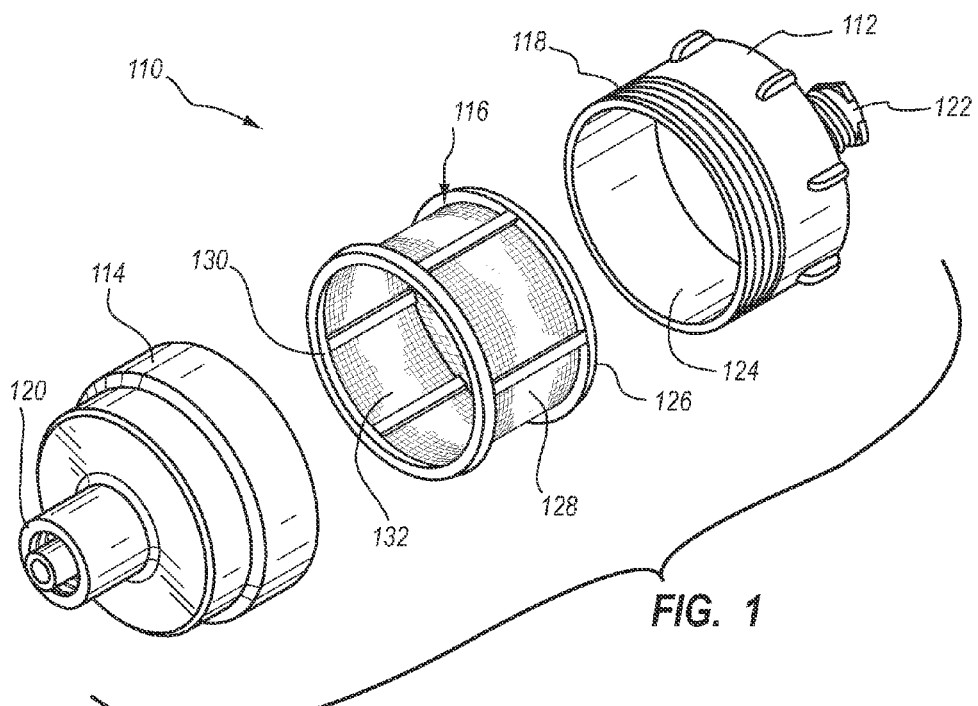
FIG. 1 is an exploded perspective view of one embodiment of a biopsy collection device for use in connection with an aspiration device.

It will be readily understood that the components of the embodiments as generally described and illustrated in the Figures herein could be arranged and designed in a wide variety of different configurations. Thus, the following more detailed description of various embodiments, as represented in the Figures, is not intended to limit the scope of the invention, as claimed, but is merely representative of various embodiments. While the various aspects of the embodiments are presented in drawings, the drawings are not necessarily drawn to scale unless specifically indicated.

The phrases "connected to," "coupled to" and "in communication with" refer to any form of interaction between two or more entities, including mechanical, electrical, magnetic, electromagnetic, fluid, and thermal interaction. Two components may be coupled to each other even though they are not in direct contact with each other. For example, two components may be coupled to each other through an intermediate component.

The use of biopsies for pathological review has become an effective manner for physicians to definitively diagnose disease and the state of illness in a patient. A typical procedure for collecting biopsies involves taking a biological sample from a patient, such as from the patient's vasculature, through the use of an aspiration device. Once aspirated, the biological sample is then expelled from the aspiration device onto a filter to collect the more viscous biological sample separated from the body fluid of the patient. The specimen is then prepared for analysis and analyzed by a hospital's pathology department or similar laboratory.

Conventional methods relating to the handling of biopsy specimens may be problematic due to the breakdown of samples in the collection process. For example, after aspirating a biological sample into a syringe, the sample may degrade through the turbulent flow of expelling the sample onto a filter. This may result in biopsies of insufficient quality for pathological analysis. Furthermore, expelling a sample with body fluids may result in a greater likelihood of biohazard exposure to a clinician.

The biopsy collection device and related methods disclosed herein provide a mechanism to maintain the integrity of a biological sample by potentially eliminating the step of expelling the biological sample from the aspiration device. One embodiment of a device and method is disclosed herein where a biological sample is collected in a filter located distally and in fluid communication with an aspiration device such that the sample is collected in the filter and not subjected to or degraded by turbulent flow by expelling it from the aspiration device, such as a vacuum syringe.

In one exemplary embodiment, the removal and analysis of a biological sample from a patient may be more effective and reliable than conventional methods by filtering the biological sample from the body fluid (which may include blood) as the sample is withdrawn from the biopsy site within the vasculature of a patient.

FIG. 1 represents one embodiment of a biopsy collection device 110 as shown from an exploded perspective view. The biopsy collection device 110 shown comprises a filter capsule with a proximal portion 112 that may be coupled to a distal portion 114 to form a filter capsule housing which encloses a filter 116. The proximal portion 112 and distal portion 114 may be coupled together through a threaded engagement 118. In other embodiments, the proximal 112 and distal 114 portions are coupled together through a snap, detent or latch mechanism, or alternatively through an interference fit.

The distal portion 114 includes a distal port 120 that is a male component and can accept a female luer connector that is in fluid communication with a lumen that in turn is in fluid communication with a body cavity of a patient, such as the patient's vasculature. Alternatively, the distal port 120 may be a female component that couples with a male luer connector. Furthermore, the distal port 120 may be a connector other than a luer connector.

The proximal portion 112 includes a proximal port 122 that is a female component and can accept a male luer connector that is in fluid communication with an aspiration device, such as a vacuum syringe. Alternatively, the proximal portion 122 may be a male component that couples with a female luer connector. Furthermore, the proximal port 122 may be a connector other than a luer connector.

The proximal 112 and distal 114 portions of the biopsy collection device 110 define a chamber volume 124 which can accommodate the filter 116. The filter 116 is configured to fit within the chamber volume 124 of the filter housing of the biopsy collection device 110. The filter 116 includes a base 126 with side walls 128 and an open end 130 that is opposite the base 126. The base 126 and side walls 128 of the filter 116 define a collection volume 132. The collection volume 132 provides a space through which the biological sample may pass into, comingled with body fluids as it enters the biopsy collection device 110 via the distal port 120. As the biological sample enters the collection volume 132 of the filter 116, a screen of the filter 116 prevents the passage of the relatively more solid biological sample and allows the body fluid to pass through the filter 116 and out the proximal port 122 toward the aspiration device. The biological sample remains in the collection volume 132 and may be accessed for pathological analysis by separating the distal portion 114 from the proximal portion 112 without the need to expel the biological sample out of the distal port 120 under turbulent flow.

In one embodiment, the side walls 128 and the base 126 comprise a screen. The mesh size of the screen at the base 126 may be the same mesh size of the screen along the side walls 128. In another embodiment, the base 126 comprises a screen while the side walls 128 are impervious to fluid flow. In one embodiment, the screen of the side walls 128 and base 126 may have a mesh size that is finer than about 40 mesh. In another embodiment the screen may have a mesh size that is finer than about 70 mesh. In yet another embodiment, the screen may have a mesh size that is between about 30 mesh and about 80 mesh. In one particular example, the mesh size of the screen is about 40 mesh. In another particular example, the mesh size of the screen is about 70 mesh. For example, a screen having a mesh size of 40 mesh would prevent the passage of particles having a particle size larger or courser than 40 mesh, but would pass particles and fluid that are finer than 40 mesh.

Referring still to FIG. 1, the filter 116 seats in the proximal portion 112 of the biopsy collection device 110 with the base 126 oriented toward the proximal port 122 and the open end 130 of the filter 116 oriented toward the distal portion 114 of the filter housing. In one embodiment, the filter 116 is cylindrical in shape to conform to the cylindrical housing of the biopsy collection device 110. The cylindrical filter 116 has a circular base 126 and cylindrical side walls 128. The filter 116 may be removable from the filter housing of the biopsy collection device 110 so a medical professional or technician may be able to easily access the biological sample once it has been collected for pathological analysis.

Figure 2:
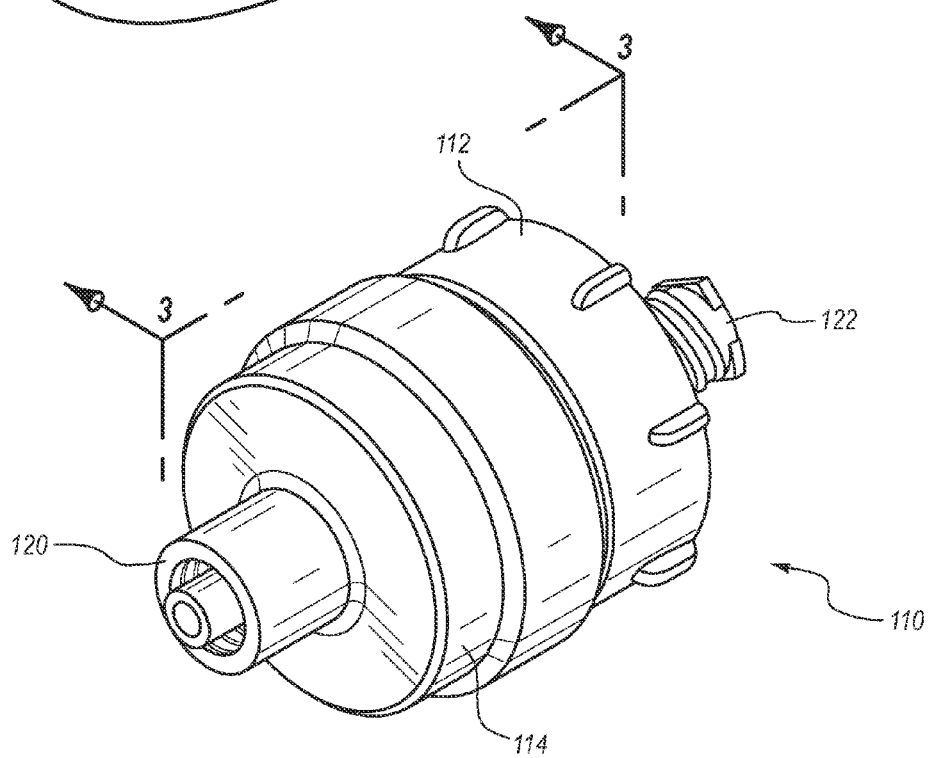
FIG. 2 is a perspective view of the biopsy collection device of FIG. 1.

FIG. 2 is a perspective view of the biopsy collection device 110 of FIG. 1, with the proximal portion 112 and the distal portion 114 in sealing engagement with each other. The filter (not shown) is disposed within the chamber volume created by the union of the proximal 112 and distal 114 portions. Once the proximal 112 and distal 114 portions are coupled together, a biological sample accompanied by fluid may pass through the distal port 120 into the chamber volume which contains the filter. The biological sample is contained within the collection volume defined by the filter and the remaining fluid can exit the biopsy collection device 110 through the proximal port 122 toward the aspiration device.

Figure 3:
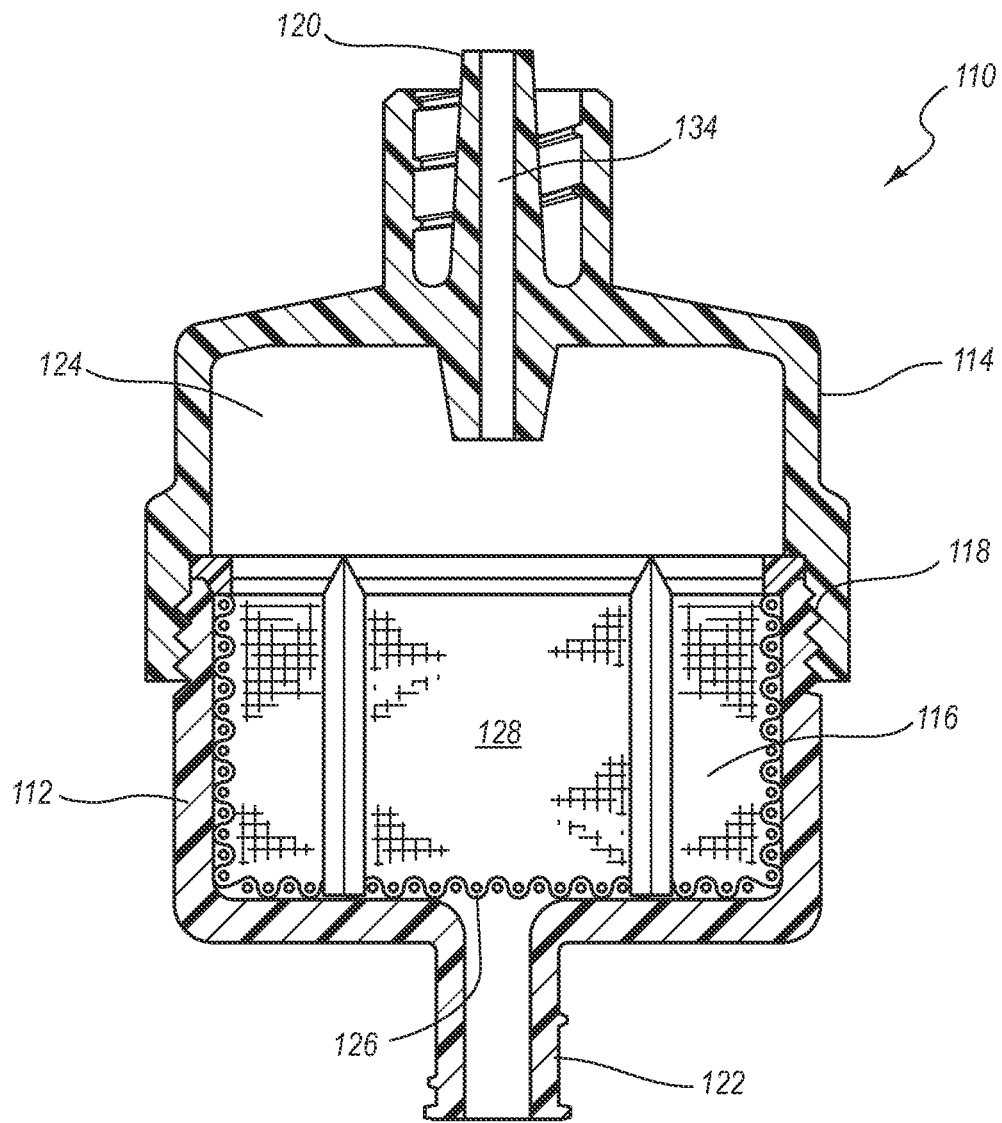
FIG. 3 is a cross-sectional side elevation view of the biopsy collection device of FIG. 2 shown along plane 3-3.

FIG. 3 is a cross-sectional side elevation view of the biopsy collection device 110 of FIG. 2, as shown along plane 3-3. The biopsy collection device 110 includes the proximal portion 112 with the proximal port 122 comprising a female connector. The proximal portion 112 is releaseably and sealingly coupled (optionally by a threaded coupling 118) to the distal portion 114 having a distal port 120 comprising a male connector. Together the proximal 112 and distal 114 portions create a filter housing and the proximal 112 and distal 114 portions define a chamber volume 124. Within the chamber volume 124 the filter 116 seats in the proximal portion 112. The filter 116 includes the base 126 and side walls 128 which comprise a filter screen that defines a collection volume. The proximal port 122 is configured to be in fluid communication with an aspiration device, so that a biological sample comingled with body fluid is aspirated through a lumen coupled to the distal port 120. The biological sample flows through a lumen 134 of the distal port 120 and into the chamber volume 124 where it is filtered in the collection volume of the filter 116.

Figure 4:
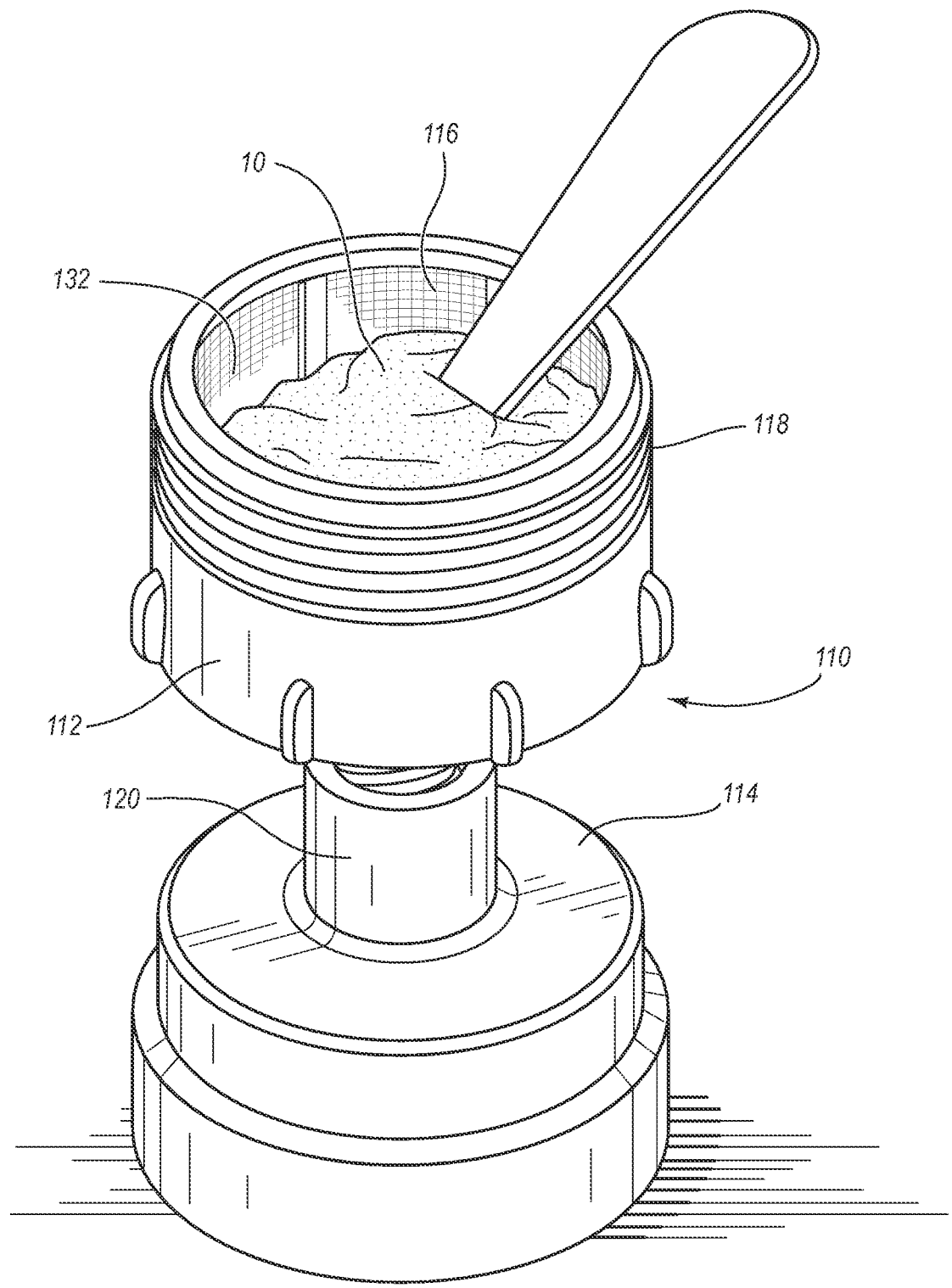
FIG. 4 is a perspective view of the biopsy collection device of FIG. 1 in a converted stand configuration, as shown with a biological sample disposed therein.

FIG. 4 is a perspective view of the biopsy collection device 110 of FIG. 1 in a converted stand configuration after collection of a biological sample 10. The biological sample 10 is collected into the collection volume 132 of filter 116 as described herein in connection with FIGS. 1-3. Once the biological sample 10 has been collected, the biopsy collection device 110 is disconnected from the lumen in fluid communication with the patient and is disconnected from the aspiration device. The distal portion 114 may be separated from the proximal portion 112, for example by unthreading the threaded engagement 118 of distal 114 and proximal 112 portions.

The proximal portion 112 is kept upright so that the biological sample 10 is maintained in the collection volume 132. In one embodiment, the connectors at the proximal 122 and distal 120 ports are sized so that they may be coupled together. The distal portion 114 is then moved below the proximal portion 112 so that the male connector of the distal port 120 may threadably engage or otherwise couple to the female connector of the proximal port 122. The distal portion 114 then becomes a stand upon which the biopsy collection device 110 may be stabilized on a surface in a converted stand configuration. The biological sample 10 may then be accessed by a medical professional or technician for pathological analysis, for example through the use of a spatula.

Figure 5:
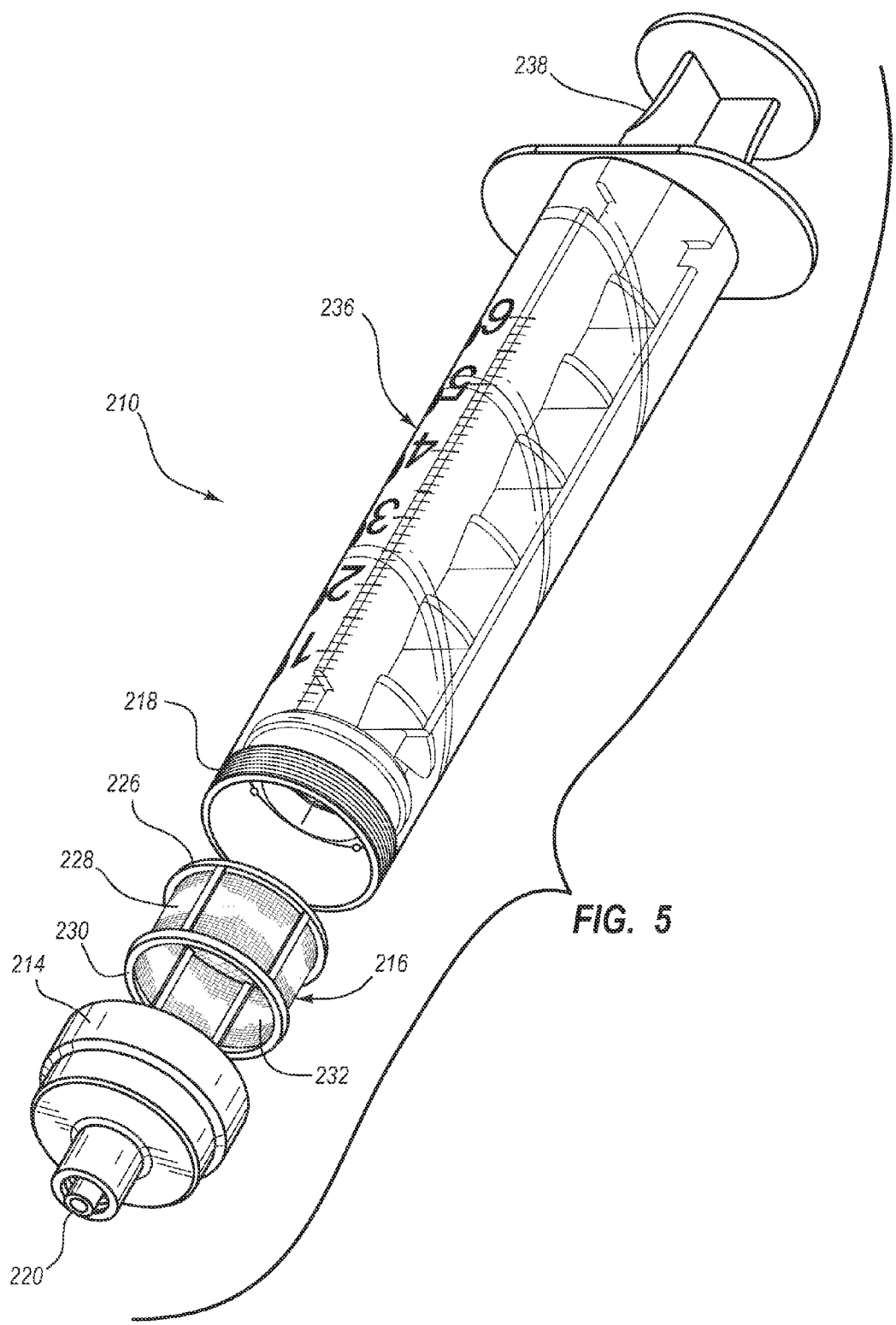
FIG. 5 is an exploded perspective view of another embodiment of a biopsy collection device which includes an aspiration device.

FIG. 5 is an exploded perspective view of another embodiment of a biopsy collection device 210. In this embodiment, the biopsy collection device 210 includes a syringe 236 which can provide a vacuum or negative pressure sufficient to aspirate a biological sample from the body of a patient. The syringe 236 may be in fluid communication with a lumen that is positioned within the body of a patient. A negative gauge pressure is provided when a clinician draws the plunger 238 of the syringe 236 in a proximal direction.

The plunger 238 of the syringe 236 may include a selective locking component where the plunger 238 can be selectively positioned into and out of a locked position through the use of spaced apart flanges along the length of the stem of the plunger 238. The selective locking component may include a stop member on the barrel of the syringe 236 projecting inwardly to selectively engage the spaced apart flanges along the stem of the plunger 238. The plunger 238 may be rotated to disengage the flange from the locking component.

A filter 216 is disposed within a distal portion of the housing of the syringe 236. The filter 216 may be similar to the filter embodiments described in connection with FIGS. 1-4. For example, the filter 216 is configured to fit within the distal portion of the syringe 236 housing. The filter 216 includes a base 226 with side walls 228 that define a collection volume 232 and an open end 230 that is opposite the base 226. The side walls 228 and the base 226 may comprise a screen with a mesh size as described in connection with FIGS. 1-4.

At the distal end of the biopsy collection device 210 an end cap 214 may be coupled to the syringe 236 via a threaded engagement 218 or other similar coupling method as described herein. The end cap 214 includes a distal port 220 which is configured to be in fluid communication with a lumen that is disposed within a body of a patient.

When a clinician applies a vacuum by actuating the syringe 236, a biological sample may be drawn through the distal port 220 and into the collection volume 232 of the filter 216. The filter 216 prevents the passage of the relatively more solid biological sample and allows the body fluid to pass through the filter 216 and into the main volume of the syringe 236 that has been made available by proximal actuation of the plunger 238. The biological sample remains in the collection volume 232 and may be accessed for pathological analysis by separating the end cap 214 from the syringe 236 without the need to expel the biological sample out of the distal port 220 under turbulent flow.

Figure 6:
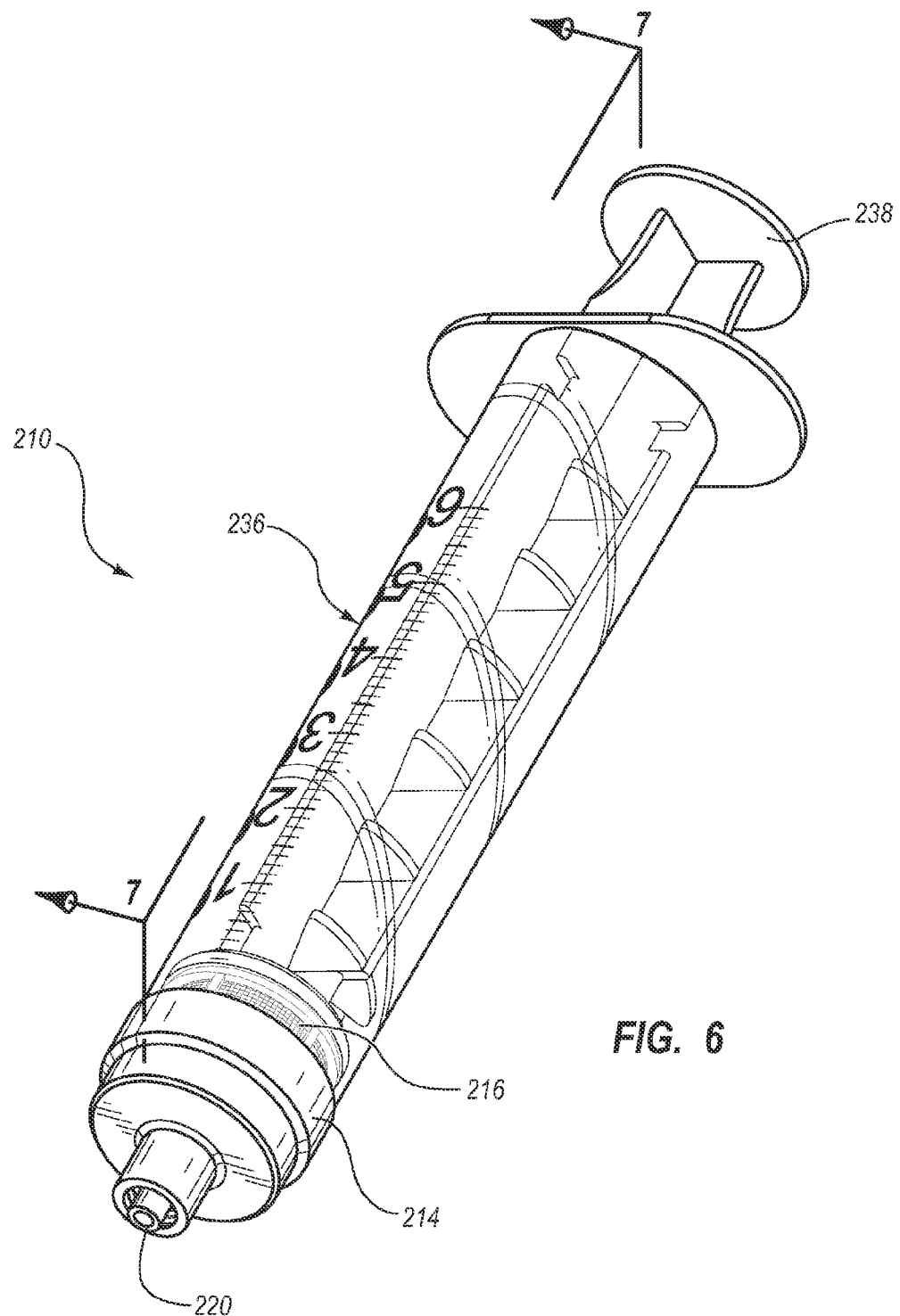
FIG. 6 is a perspective view of the biopsy collection device of FIG. 5.
Figure 7:
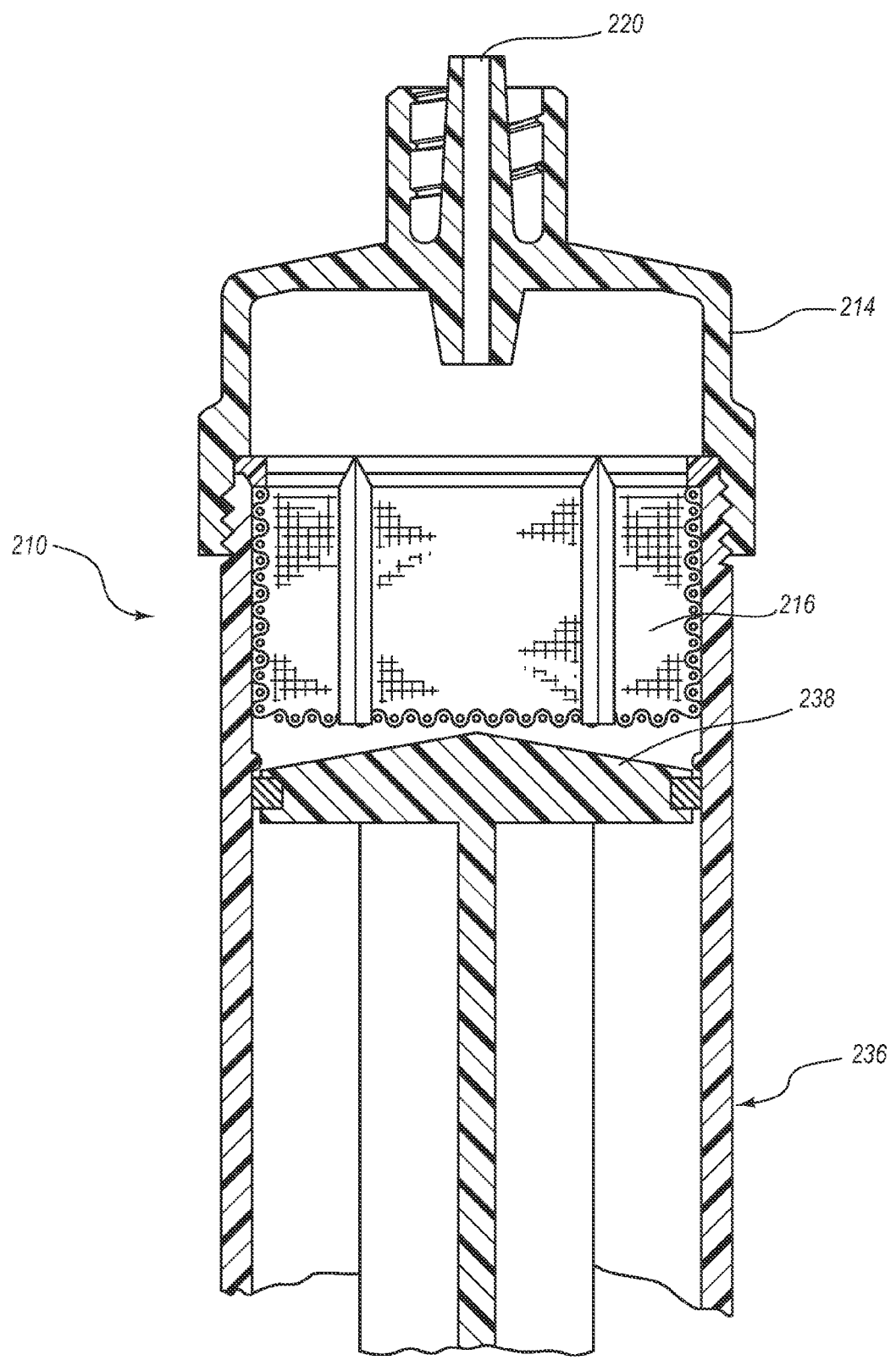
FIG. 7 is a cross-sectional side elevation view of the biopsy collection device of FIG. 6 shown along plane 7-7.

FIGS. 6 and 7 represent the biopsy collection device 210 of FIG. 5. FIG. 6 demonstrates the biopsy collection device 210 from a perspective view, and FIG. 7 represents the biopsy collection device 210 from a partially cut-away side elevation cross-sectional view along the plane 7-7. The end cap 214 and the syringe 236 are in sealing engagement with each other. The filter 216 is disposed within the distal portion of the syringe 236.

Figure 8:
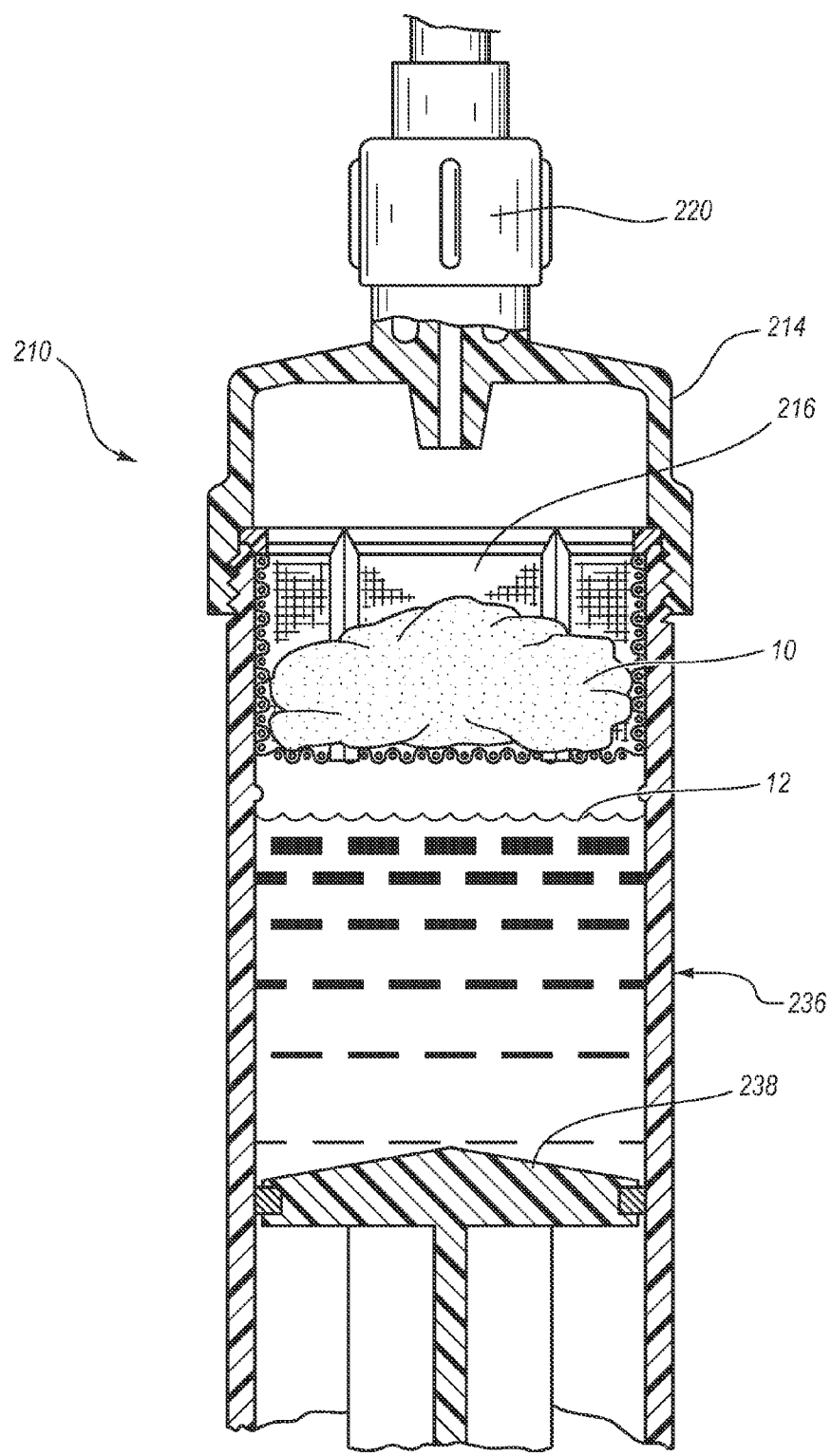
FIG. 8 is a partially cut-away cross-sectional side elevation view of the biopsy collection device of FIG. 7 as shown with a biological sample disposed therein.

FIG. 8 represents the biopsy collection device 210 of FIG. 7 in a partially cut-away cross-sectional side elevation view with a biological sample 10 disposed therein. When creating a vacuum through actuation of the plunger 238 of the syringe 236 in a proximal direction, the biological sample 10 accompanied by fluid 12 may pass through the distal port 220 into the collection volume of the filter 216. The biological sample 10 is contained within the collection volume defined by the filter 216 and the remaining fluid 12 moves into the body of the syringe 236 between the filter 216 and plunger 238. The biological sample 10 may be accessed for pathological analysis by separating the end cap 214 from the syringe 236 without the need to expel the biological sample 10 out of the distal port 220 under turbulent flow.

Figure 9:
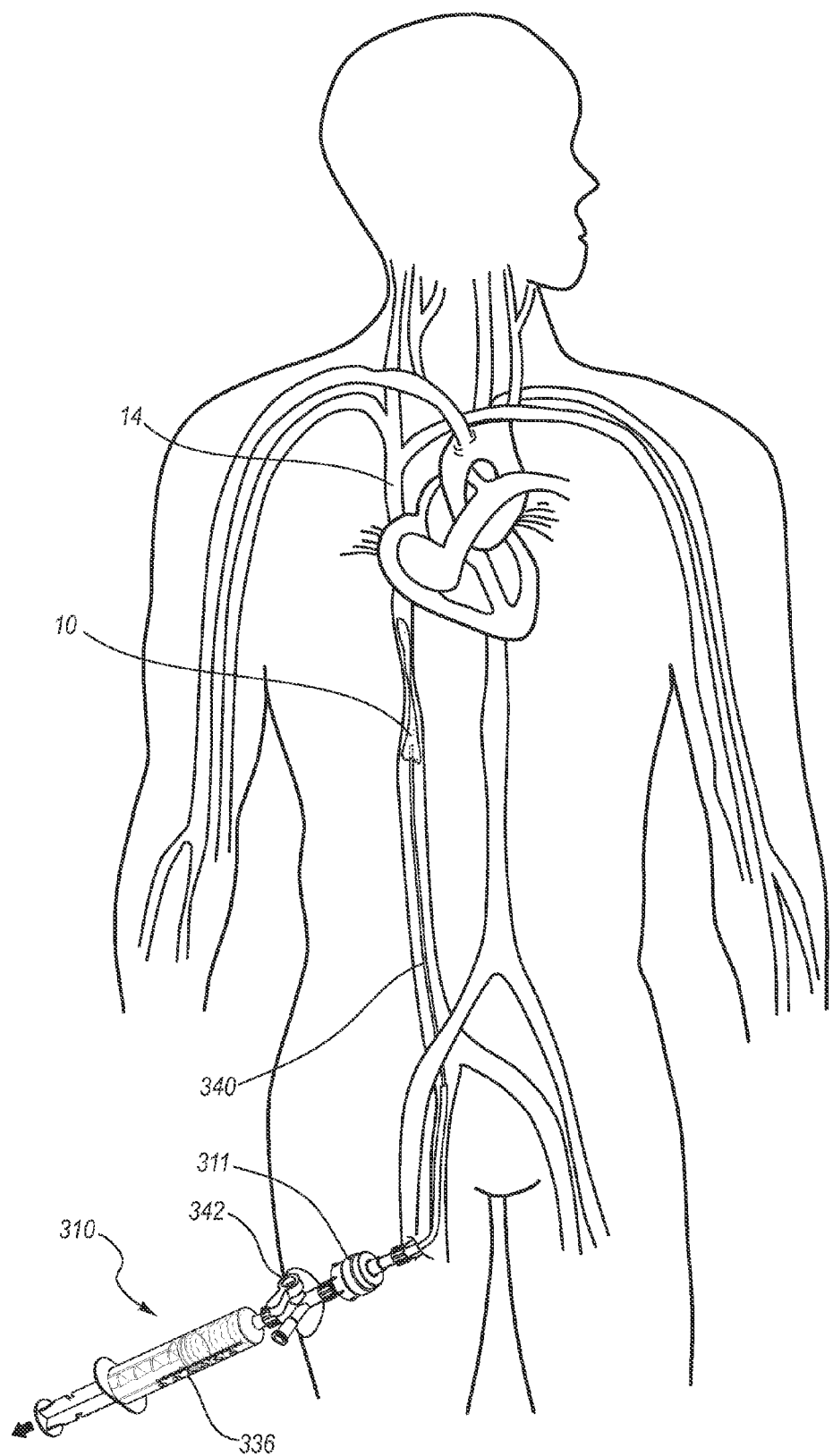
FIG. 9 is a perspective view of a biopsy collection assembly in fluid communication with the vasculature of a patient while aspirating a biological sample.

FIG. 9 represents another embodiment of a biopsy collection assembly 310 in fluid communication with the vasculature 14 of a patient while aspirating a biological sample 10. In this embodiment, the biopsy collection assembly 310 includes a filter capsule 311, which is in fluid communication with a lumen 340 that is disposed within the vasculature 14 of the patient. The filter capsule 311 may include the components described in connection with the biopsy collection device as described in FIGS. 1-4, such as a filter for collecting the biological sample 10 that is aspirated into the filter capsule 311 under negative pressure.

The filter capsule 311 may be located at a position distally from the syringe 336 or other aspiration device. A valve 342 may optionally be located at a position distally from the syringe 336, but proximal to the filter capsule 311. Alternatively, the valve 342 may be disposed at a position distally of both syringe 336 and filter capsule 311. Furthermore, in another embodiment a valve 342 may be integrated into the filter capsule 311 or in the distal end of the syringe 336.

With respect to the embodiment depicted in FIG. 9, the valve 342 may be actuated in an open position while aspirating a biological sample 10, which is filtered in the filter capsule 311. The filter disposed within filter capsule 311 prevents the passage of the relatively more solid biological sample 10 and allows the accompanying body fluid to pass through the filter and exit the filter capsule 311 through a proximal port, then pass through the open valve 342 and into the syringe 336. The biological sample 10 remains in the filter capsule 311 and may be accessed for pathological analysis without the need to expel the biological sample 10 out of the filter capsule 311 by applying a positive pressure.

Upon aspiration of the biological sample 10, the valve 342 may be closed to prevent the body fluid in the syringe 336 from leaking when the clinician is attempting to access the biological sample 10 from the filter capsule 311. In an alternative embodiment, the valve 342 may be self-actuating, in that the valve 342 opens when a negative pressure is applied and closes when the negative pressure ceases.

While specific embodiments of biopsy collection devices have been illustrated and described, it is to be understood that the invention claimed hereinafter is not limited to the precise configuration and components disclosed. Various modifications, changes, and variations apparent to those of skill in the art may be made in the arrangement, operation, and details of the methods and systems disclosed.

Without further elaboration, it is believed that one skilled in the art may use the preceding description to utilize the present disclosure to its fullest extent. The examples and embodiments disclosed herein are to be construed as merely illustrative and exemplary and not a limitation of the scope of the present disclosure in any way. It will be apparent to those having skill in the art that changes may be made to the details of the above-described embodiments without departing from the underlying principles of the invention as claimed hereinafter. In other words, various modifications and improvements of the embodiments specifically disclosed in the description above may be within the scope of the appended claims.

What is claimed is:

1. biopsy sample collection device, comprising:
   a filter housing, comprising:
   a proximal portion having a proximal port configured for fluid communication with an aspiration device;
   a distal portion having a distal port configured for fluid communication with a lumen positioned within a body of a patient;
   the proximal and distal portions coupleable to each other and defining a chamber volume therein, such that the distal port and proximal port are in fluid communication with each other; and
   a filter disposed within the chamber volume, the filter having a base, side walls and an open end, wherein the base and side walls define a collection volume configured for collecting biopsy sample therein as fluid flows from the distal port through the collection volume and to the proximal port;
   wherein the distal portion and the proximal portion are removable from each other, and the distal port is configured to be coupled to the proximal port, such that the distal portion is a stand upon which the proximal portion rests after collection of the biopsy sample.

2. The biopsy sample collection device of claim 1, wherein the filter is configured to seat in the proximal portion of the filter housing with the base of the filter oriented toward the proximal port and the open end of the filter oriented toward the distal portion of the filter housing.

3. The biopsy sample collection device of claim 1, wherein the distal port comprises a male component configured to accept a female luer connector and the proximal port comprises a female component configured to accept a male luer connector.

4. biopsy sample collection device of claim 1, wherein the base and side walls of the filter comprise a screen.

5. The biopsy sample collection device of claim 4, wherein the screen has a mesh size that is 40 mesh.

6. The biopsy sample collection device of claim 1, wherein the filter comprises a circular base and cylindrical side walls.

7. The biopsy sample collection device of claim 1, wherein the filter is configured to be removed from the filter housing while maintaining the biopsy sample in the collection volume.

8. The biopsy sample collection device of claim 1, wherein the distal port comprises a female component configured to accept a male luer connector and the proximal port comprises a male component configured to accept a female luer connector.

9. A biopsy collection assembly, comprising:
an aspiration device comprising a syringe in fluid communication with a flexible lumen of a length sufficient to extend distally past the waist of the patient with entry at the groin of the patient, the aspiration device configured to provide a negative gauge pressure sufficient to aspirate a biopsy sample from the vasculature of a patient; and
a filter capsule in fluid communication with the aspiration device and the lumen, and located distally of the aspiration device, the filter capsule configured to be removable from the aspiration device and the lumen, the filter capsule comprising:
a filter housing having a proximal portion with a proximal port configured for fluid communication with the aspiration device, and a distal portion with a distal port configured for fluid communication with the lumen, the lumen configured to be positioned within the vasculature of the patient, the proximal and distal portions coupled to each other and defining a chamber volume therein and the distal port and proximal port are in fluid communication with each other;
a mesh filter disposed within the chamber volume, the filter having a base, side walls and an open end, the base oriented toward the proximal port and the open end oriented toward the distal port, wherein the base and side walls define a collection volume for collecting the biopsy sample therein, wherein the syringe is configured to cause fluid to flow through the lumen into the filter capsule and collection volume and toward the aspiration device when the syringe provides negative gauge pressure to the lumen via the filter housing, and wherein the proximal and distal portions of the filter housing are configured to be removable from each other to enable access to a biopsy sample disposed within the collection volume of the filter.

10. The biopsy collection assembly of claim 9, further comprising a valve in fluid communication with the aspiration device and filter capsule.

11. The biopsy collection assembly of claim 10, wherein the valve is disposed proximal to the filter capsule.

12. The biopsy collection assembly of claim 9, wherein the aspiration device comprises a connector having a male connection component which is coupleable to the proximal port of the filter housing which comprises a female connection component.

13. The biopsy collection assembly of claim 9, wherein the filter is configured to be removed from the filter capsule while maintaining the biopsy sample in the collection volume.

14. The biopsy collection assembly of claim 9, wherein the syringe comprises a movable plunger, the syringe including a selective locking component where the plunger is configured to be selectively positioned into and out of a locked position restricting movement of the plunger.

15. The biopsy collection assembly of claim 14, wherein the selective locking component is configured to selectively position the plunger into and out of any of a plurality of locked positions restricting movement of the plunger.

16. A method for collecting a biopsy sample, comprising:
placing a lumen into the vasculature of a patient;
applying a negative gauge pressure from a syringe in fluid communication with the lumen, to aspirate a biopsy sample comingled with blood from the vasculature of the patient;
drawing the biopsy sample with blood from the patient into a filter capsule via the lumen, the filter capsule comprising a distal portion coupled to the lumen, a proximal portion coupled to the syringe, and a filter having a proximal base, side walls and a distal open end, the proximal base and side walls comprising a mesh screen which defines a collection volume, wherein the sample and blood are drawn into the collection volume;
passing the blood through the mesh screen and toward the syringe while collecting the biopsy sample in the collection volume; and
accessing the biopsy sample by separating the distal portion of the filter capsule from the proximal portion of the filter capsule to expose the biopsy sample in the collection volume.

17. The method of claim 16, further comprising removing the filter with the biopsy sample after separating the distal portion of the filter capsule from the proximal portion of the filter capsule.

* * * * *